United States Patent [19]
Ishida

[11] Patent Number: 6,107,072
[45] Date of Patent: Aug. 22, 2000

[54] THERMOSTABLE GERANYLGERANYL DIPHOSPHATE SYNTHASE

[75] Inventor: Chika Ishida, Nishikamo-gun, Japan

[73] Assignee: Toyota Jidosha Kabushiki Kaisha, Toyota, Japan

[21] Appl. No.: 08/733,837

[22] Filed: Oct. 18, 1996

[30] Foreign Application Priority Data

Oct. 19, 1995 [JP] Japan ................................. 7-294956

[51] Int. Cl.[7] .............................. C12N 1/13; C12N 9/10; C12N 15/54
[52] U.S. Cl. ...................... 435/193; 435/320.1; 435/325; 435/252.3; 536/23.2
[58] Field of Search .................... 435/69.1, 71.1, 435/131, 172.1, 194, 320.1, 252.3, 193, 325; 536/23.2

[56] References Cited

U.S. PATENT DOCUMENTS 5,429,939  7/1995  Misawa et al. ............................ 435/67

FOREIGN PATENT DOCUMENTS 674000  9/1995  European Pat. Off. .

OTHER PUBLICATIONS

Hoshino et al (1993) Appl. Envir. Microb. 59:3150–3153 "Molecular cloning and sequence analysis of the crtB gene . . . ".
Misawa et al. *J. Bacteriology* 172(12):6704–6712 (1990).
Taylor et al. *J. Bacteriology* 154(2):580–590 (1983).
Chen et al. *J. Biol. Chem.* 268(15):11002–11007 (1993).
Tachibana et al. *Biosci Biotech. Biochem.* 57(7):1129–1133 (1993).
Brinkhaus et al. *Achives of Biochemistry & Biophysics* 266(2):607–612 (1988).
Michalowski et al. *J. Biol. Chem.* 266(18):11866–11870 (1991).
Kuntz et al. *The Plant Journal* 2(1):25–34 (1992).
Caratolli et al. *J. Biol. Chem.* 266(9):5854–5859 (1991).
Scolnik et al. *Plant Physiol.* 104:1469–1470 (1994).
Aitken et al. *Plant Physiol.* 108:837–838 (1995).
Jiang et al. *J. Biol. Chem.* 270(37):21793–21799 (1995).
Lang et al. *J. Bacteriology* 177(8):2064–2073 (1995).
Armstrong et al. *Mol. Gen. Genet.* 216:254–268 (1989).
Armstrong et al. *PNAS* 87:9975–9979 (1990).
Combined Meeting of 69th Biochemistry Association of Japan and 19th Molecular Biology Associate of Japan (Aug. 26, 1996).
Proceedings National Academy of Sciences USA, vol. 89, 1992, pp. 6761–6764, XP002030963, S.K. Math, et al., "The crtE gene in *Erwinia herbicola* encodes geranylgeranyl diphosphate synthase", (whole article).
Journal of Biological Chemistry, vol. 269, No. 20, 1994, pp. 14792–14797, XP002030964, S. Ohnuma, et al., "Archaebacterial ether linked lipid biosynthetic gene", (whole article).

*Primary Examiner*—Dian C. Jacobson
*Attorney, Agent, or Firm*—Kenyon & Kenyon

[57] ABSTRACT

The present invention discloses a heat-resistant geranylgeranyl diphosphate synthase originating in *Thermus thermophilus*, along with its production process and its method of use.

8 Claims, 2 Drawing Sheets

THERMOSTABLE GERANYLGERANYL DIPHOSPHATE SYNTHASE

BACKGROUND OF INVENTION

1. Field of Invention

The present invention relates to a novel geranylgeranyl diphosphate synthase, process for production thereof, a gene system coding for said enzyme, and a process for producing geranylgeranyl diphosphate using said enzyme.

2. Related Art

Among known isoprenoids (the generic name for substances having the basic skeleton of $(C_5H_8)_n$) of various chain lengths, geranylgeranyl diphosphate (GGPP) in particular, having a chain length of 20 carbon atoms, is highly valuable in industrial uses as a starting material for terpenoids having various useful physiological activities as well as vitamins A, K and E. Although this GGPP having a high industrial usefulness is manufactured by chemical synthesis, it is extremely expensive due to the extremely low yield.

On the other hand, prenyl transferase is known as an enzyme that synthesizes isoprenoids of various chain lengths using as starting materials, isopentenyl diphosphate (IPP) and allylic diphosphates. Geranylgeranyl diphosphate synthase in particular mainly synthesizes GGPP. Thus, if it was possible to increase the yield of GGPP by using this enzyme reaction, it is expected that GGPP would be able to be manufactured inexpensively. Since by using this enzyme reaction, only the trans-form is synthesized, this enzymatic method is advantageous over chemical synthesis methods in which the cis-form, which is difficult to be separated, is produced as a by-product.

Until now, genes for GGPP synthase (GGPS) were known to be derived from a plant pathogen, *Erwinia uredovora*, a soil bacterium, *Myxococcus xanthus*, a red bread mould, *Neurospora crassa* and so forth. Some of them are expressed in *Escherichia coli*. However, since none of these enzymes have thermostable, enzyme activity has poor stability. Since these enzymes are unable to be used stably for long periods of time in industrial applications, there has been a need for a more stable enzyme.

GGPP synthase derived from a highly thermophilic bacteria, *Sulfolobus acidocardarius*, has already been reported in response to this need. Although enzyme derived from *Sulfolobus acidocardarius* has higher stability than other known enzymes, it has a problem of a low specific activity. In addition, the GGPP synthase derived from a methane-producing bacterium, *Methanobacterium thermoautotrophicum*, has also been reported as an enzyme having a high thermostability. In this report, the enzyme productivity per cell is so low that it is not practical.

Thus, since there is no geranylgeranyl diphosphate synthase that can be used industrially, the development of a practically useful enzyme is desired.

SUMMARY OF THE INVENTION

Thus, the object of the present invention is to provide a geranylgeranyl diphosphate synthase that is highly stable and thermoresistant, enabling it to be used stably for a long time in industrial applications, process for production thereof, a gene system for said enzyme, and a process for producing geranylgeranyl diphosphate using said enzyme.

As a result of earnest studies to achieve the above-mentioned object, the inventors of the present invention completed the present invention by cloning a gene for GGPP synthase from *Thermus thermophilus*, that has a high enzyme activity and produces few by-products, introducing the gene into a microorganism such as *E. coli*, and expressing the enzyme in large amount.

Thus, the present invention firstly provides a geranylgeranyl diphosphate synthase having the amino acid sequence indicated in SEQ ID NO. 6, or an amino acid sequence modified by addition and/or deletion of one or amino acids and/or substitution with other amino acids with respect to said amino acid sequence.

Secondly, the present invention provides DNA coding for the above-mentioned geranylgeranyl diphosphate synthase, a vector and particularly an expression vector that contains said DNA, and a host transformed with said vector.

Thirdly, the present invention provides a process for producing geranylgeranyl diphosphate synthase by culturing the above-mentioned host, and recovering the above-mentioned geranylgeranyl diphosphate synthase from said culture.

Fourthly, the present invention provides a process for producing geranylgeranyl diphosphate by allowing the above-mentioned enzyme to act on one or more prenyl diphosphates having 15 or less carbon atoms.

MODE OF CARRYING OUT THE INVENTION

Figure 1:
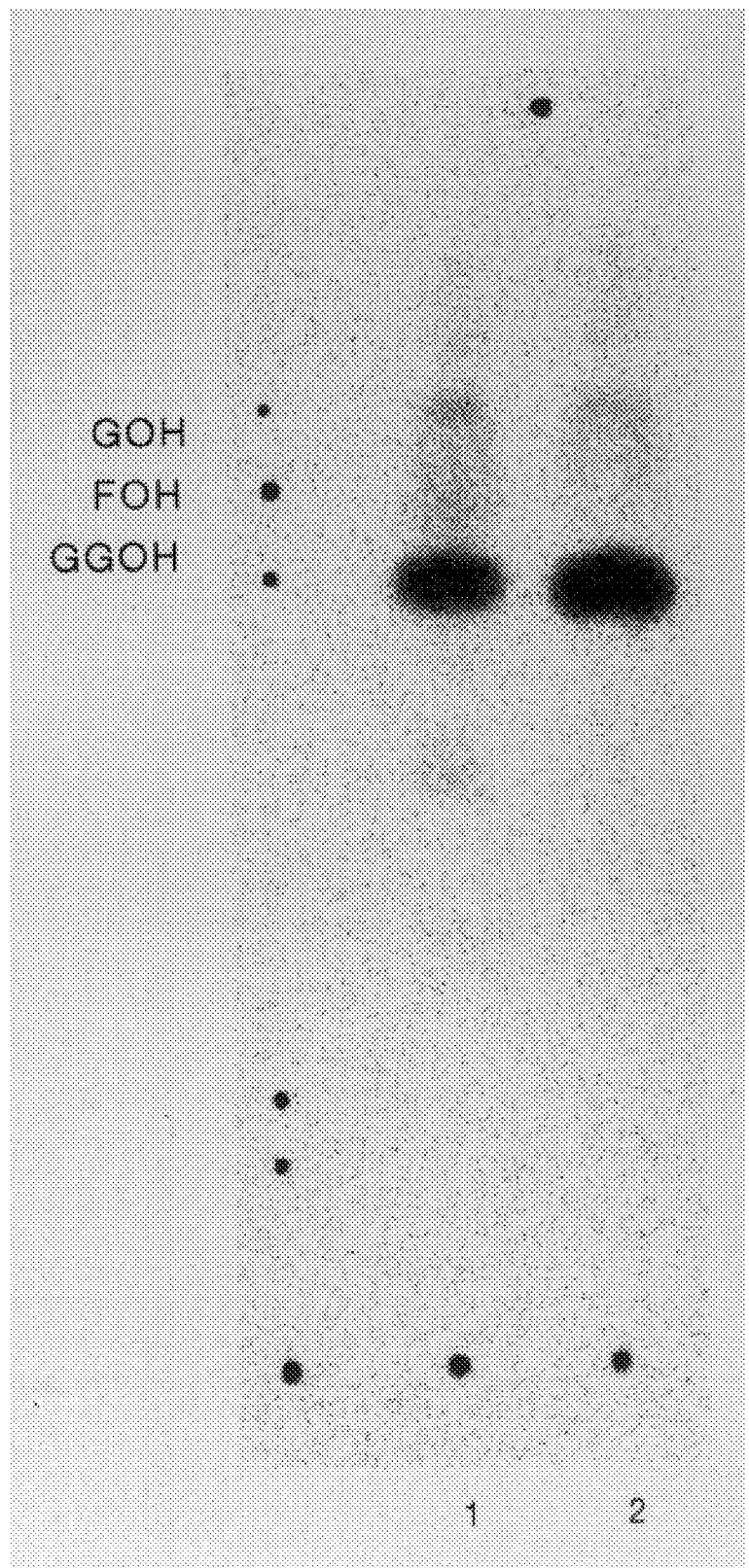
FIG. 1 shows a photograph of a thin layer chromatography resulting from the analysis of the product that is formed by allowing geranylgeranyl diphosphate synthase expressed from plasmid pTE3 (GGPS) to act on substrates farnesyl diphosphate (FFP:2) or dimethylallylic diphosphate (DMAPP:1), and isopentenyl diphosphate (IPP). FOH indicates farnesol, while GGOH indicates geranylgeraniol.
Figure 2:
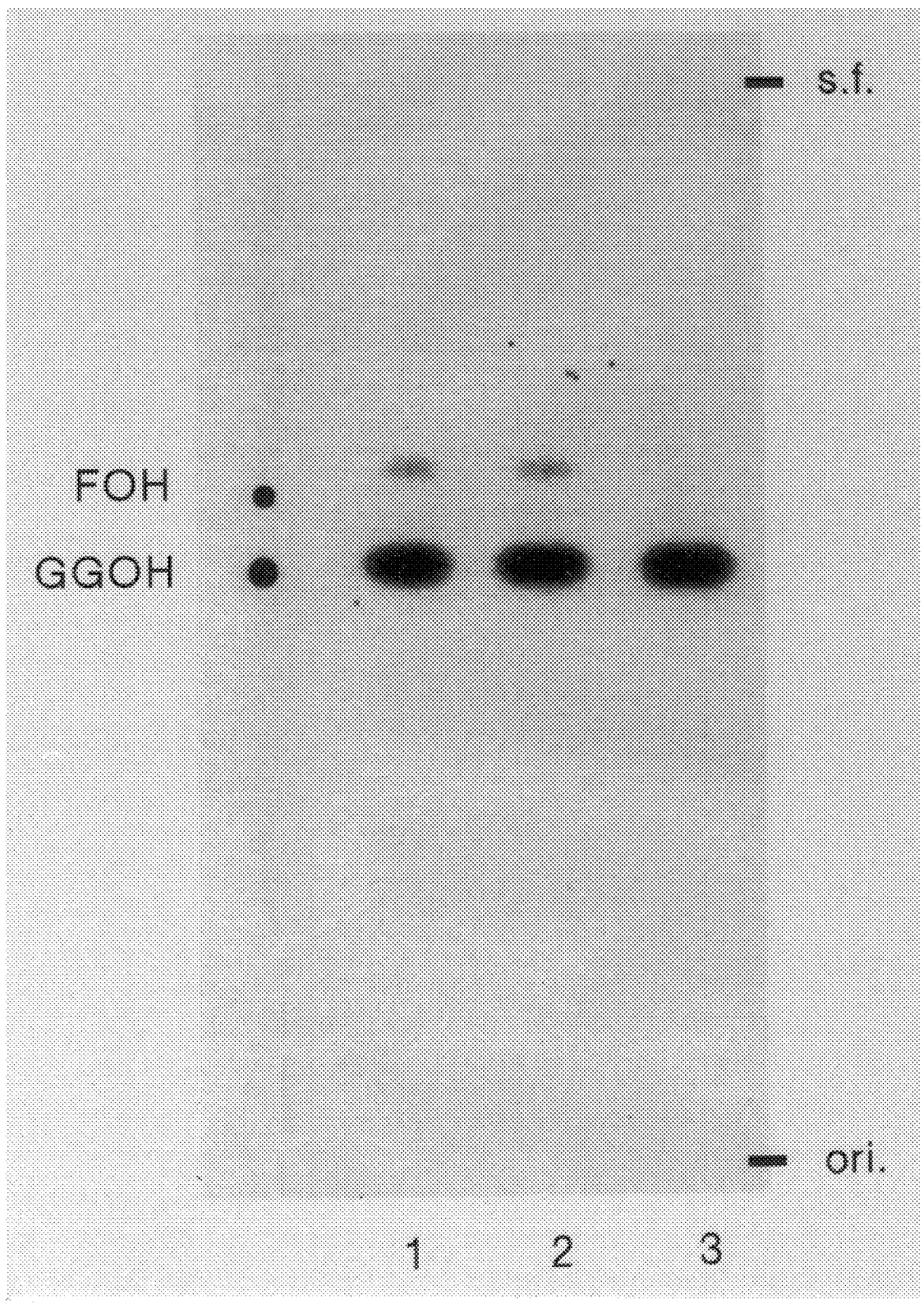
FIG. 2 shows a photograph of a thin layer chromatography resulting from the analysis of the product that is formed by allowing an enzyme, which is produced by expressing the geranylgeranyl diphosphate synthase (GGPS) of the present invention in the form of a fused protein with glutathione S transferase, treating with thrombin and purifying the GGPS portion, to act on substrates dimethylallylic diphosphate (DMAPP:1), geranyl diphosphate (GPP:2) or farnesyl diphosphate (FPP:3), and isopentenyl diphosphate (IPP). GOH indicates geraniol, FOH indicates farnesol, and GGOH indicates geranylgeraniol.

According to the present invention, DNA is prepared from the chromosomes of a thermophilic microorganism, *Thermus thermophilus*. Although any strain belonging to the species *Thermus thermophilus* may be used, ATCC strain 27634, which is available from ATCC, can also be used. After preparing chromosomal DNA in accordance with a conventional method, the resulting DNA is cleaved with a suitable restriction enzyme and inserted into a suitable vector to construct a DNA library. Screening of this DNA library should be designed based on the amino acid sequence of a known geranylgeranyl diphosphate synthase. An example of a particular method for this is shown in Example 1.

Although a typical amino acid sequence of the enzyme of the present invention is as shown in SEQ-ID NO.6, this amino acid sequence may be modified.

It is known that there is a case wherein an enzyme is modified by addition, deletion and/or substitution of one or more amino acids in comparison with the amino acid sequence that exists in nature, the modified amino acid sequence still possesses its inherent enzyme activity. Thus, in addition to the peptide having the amino acid sequence shown in SEQ ID NO.6, the present invention also includes enzymes that are still able to demonstrate their native biological activity while having an amino acid sequence wherein 1 or a small number of amino acids, such as 5, or 10, 20 or 30 amino acids, have been substituted, deleted and/or added to the amino acid sequence shown in SEQ ID NO.6.

In addition, the present invention also provides a gene coding for the above-mentioned various enzymes including modified enzymes, a vector and particularly an expression vector containing that gene, and a host transformed with said vector. The gene (DNA) of the present invention can be easily obtained cloning it from the genome of *Thermus thermophilus,* or by introducing a mutation into, for example, the DNA that codes for the naturally-occurring amino acid sequence shown in SEQ ID NO.6 in accordance with a conventional method such as site-specific mutagenesis or PCR.

Although the nucleotide sequence of a gene of the present invention is the nucleotide sequence shown in SEQ ID NO:1 as well as that which codes for the above-mentioned various amino acid sequences, DNA is also included in the present invention that codes for a polypeptide having geranylgeranyl diphosphate synthase activity and is hybridized with a DNA having the nucleotide sequence shown in SEQ ID NO:1, under the hybridization conditions of a hybridization medium (5×SSC, blocking reagent 1% (w/v), N-lauroylsarcosine 0.1% (w/v) and SDS 0.02% (w/v) where the composition of 20×SSC consists of an aqueous solution of 3 mol of NaCl and 0.3 mol of sodium citrate in 1 liter).

Once the target amino acid sequence of the enzyme has been determined, a suitable nucleotide sequence coding for that amino acid sequence can also be determined, and DNA can be chemically synthesized in accordance with a conventional DNA synthesis method.

In addition, the present invention also provides an expression vector that contains said DNA, hosts transformed with said expression vector, and a process for producing the enzyme or peptide of the present invention using said host.

Although an expression vector contains an origin of replication, expression control sequences and so forth, they differ depending on the host. Examples of hosts include procaryotes such as bacteria, examples of which include *E. coli* and Bacillus species such as *Bacillus subtilis,* eucaryotes such as fungi and yeasts, examples of which include *Saccharomyces cereviseae* belonging to the genus Saccharomyces and *Pichia pastoris* belonging to the genus Pichia, molds, examples of which include the genus Aspergillus, of example, *Aspergillus oryzae* and *Aspergillus niger,* and animal cells, examples of which include cultured silkworm cells and cultured cells of higher animals such as CHO cells.

In an example of using *E. coli* for the host, gene expression regulatory functions are known to exist such as in the process of transcribing mRNA from DNA and the process of translating protein from mRNA. In addition to those sequences present in nature (e.g. lac, trp, bla, lpp, $P_L$, $P_R$, ter, T3 and T7), sequences in which their mutants (e.g. lacUV5) are artificially joined with naturally-occurring promoter sequences (e.g. tac, trc) are known as examples of promoter sequences that regulate mRNA synthesis, and they can also be used in the present invention.

It is known that the sequence of ribosome binding site (GAGG and other similar sequences) and the distance from the ribosome binding site to the starting codon such as ATG are important as factors that regulate the ability to synthesize proteins from mRNA. In addition, it is also well known that the terminator, which commands termination of transcription on the 3'-side (e.g. a vector containing $rrnPT_1T_2$ is commercially available from Pharmacia), has an effect on protein synthesis efficiency in the recombinant.

Although commercially available vectors as such can be used as a starting vector for the construction of recombinant vectors of the present invention, various types of vectors derived according to the specific purpose can also be used. Examples of them include pBR322, pBR327, pKK223-3, pKK233-2 and pTrc99, having a replicon of pMB1 origin; pUC18, pUC19, pUC118, pUC119, pBluescript, pHSG298 and pHSG396, modified to improve the number of copies; pACYC177 and pACYC184, having a replicon of p151A origin; as well as plasmids derived from pSC101, ColE1, R1, or F factor. Moreover, expression vectors for fused proteins that are easier to be purified can also be used, examples of which include pGEX-2T, pGEX-3X and pMal-c2.

In addition, introduction of a gene to a host can also be performed by using virus vectors or transposons such as λ-phages and M13 phages, in addition to plasmids. As a case of introduction of gene into a microorganism other than *E. coli,* introduction of a gene into Bacillus sp. is known using pUB110 (sold by Sigma) or pHY300PLK (sold by Takara Shuzo). These vectors are described in Molecular Cloning (J. Sambrook, E. F. Fritsch, T. Maniatis ed., Cold Spring Harbor Laboratory Press, pub.), Cloning Vector (P. H. Pouwels, B. E. Enger Valk, W. J. Brammar ed., Elsevier pub.) and various company catalogs.

In particular, pTrc99 (sold by Pharmacia) has Ptrc and $lacI^q$ as promoter and control gene, the sequence AGGA for the ribosome binding site, and $rrnPT_1T_2$ for the terminator in addition to an ampicillin-resistant gene for the selection marker, thus making it a preferable example of a vector having an expression regulatory function for the HDP synthase gene.

Incorporation of a DNA fragment coding for geranylgeranyl diphosphate synthase and, as necessary, a DNA fragment having the function of regulating expression of the gene of above-mentioned enzyme, into these vectors can be performed according to known methods using a suitable restriction enzyme and ligase. Specific examples of plasmids of the invention prepared in this manner include pTE3, pTE7 and pTE20.

Examples of microorganisms that can be used for gene introduction with this type of recombinant vector include *E. coli* and Bacillus sp. The transformation can also be performed according to a conventional method such as the $CaCl_2$ method or protoplast method described in Molecular Cloning (J. Sambrook, E. F. Fritsch, T. Maniatis ed., Cold Spring Harbor Laboratory Press pub.) and DNA Cloning Vol. I-III (D. M. Glover ed., IRL Press pub.).

In producing the enzyme of the present invention, the above-mentioned transformed host is cultured after which the enzyme can be recovered and purified from that culture in accordance with a conventional method, examples of which include desalting, organic solvent sedimentation, gel filtration, affinity chromatography, hydrophobic chromatography and ion exchange chromatography.

In addition, the present invention provides a process for producing geranylgeranyl diphosphate using the enzyme of the present invention. In this process, the enzyme of the present invention should be allowed to react with an allylic isoprenoid such as dimethylallylic diphosphate, in a medium, and particularly an aqueous medium, and then the target geranylgeranyl diphosphate should be harvested from the reaction medium as desired. The enzyme may not only be purified enzyme, but also crude enzymes obtained by semi-purification through various stages, or a substance containing enzyme such as cultured microbial cells or the culture itself. In addition, the above-mentioned enzyme, crude enzyme or enzyme-containing substance may be an immobilized enzyme that has been immobilized in accordance with a conventional method.

Isoprenyl diphosphate having fewer carbon atoms than the target geranylgeranyl diphosphate, for example 5 to 15 carbon atoms, and isopentenyl diphosphate are used for the substrate. Water or an aqueous buffer, such as phosphate buffer, are used for the reaction medium.

EXAMPLES

The following provides a detailed explanation of the present invention through its Examples.

Example 1

Cloning of DNA Coding for GeranylgeranylDiphosphate (1) Preparation of Chromosomal DNA of *Thermus thermophilus*

*Thermus thermophilus* strain ATCC 27634 was cultured in 697 medium described in ATCC at 75° C. Next, the chromosome was prepared in accordance with Current Protocols in Molecular Biology.

(2) Oligonucleotide Preparation

The oligonucleotides of Table 1 were designed on the basis of the known prenyl transferase amino acid sequences of the GGPS of *Sulfolobus acidocardarius*, GGPS of *Erwinia uredovora* and GGPS of *Neurospora crassa*. Since the genes of the Thermus genus are known to typically have a high GC content, codons were selected preferentially for GC as much as possible. The oligonucleotides were prepared with the Model 373A DNA synthesizer made by Perkin-Elmer.

(3) Genomic Southern Hybridization

After completely digesting 1 μg each of genomic DNA of *Thermus thermophilus* strain HB8 with four restriction enzymes (BamHI, HindIII, SacI and StuI), the DNA was subjected to electrophoresis on 0.8% agarose gel, and transferred to a nylon membrane (Amersham). Transfer was performed in accordance with a method described in Current Protocols in Molecular Biology. Next, primers 1 and 2 were labeled using the DIG labeling kit of Boehringer Mannheim, and used as probes. Hybridization was performed at 60° C. by following the manual of Boehringer Mannheim. When this chromosomal DNA was analyzed by genomic southern hybridization, that digested with SacI or StuI demonstrated a strong signal in the vicinity of 1.5 kbp, while that digested with BamHI or HindIll demonstrated a strong signal in the vicinity of 6 kbp.

(4) Preparation of *Thermus thermophilus* Gene Library

After digesting 1 μg each of chromosomal DNA with SacI or StuI respectively, the DNA was subjected to electrophoresis on 0.8% agarose gel to separate DNA fragments of about 1.5 kbp. Next, the DNA fragments about 1.5 kbp in size were collected from the gel and purified using GeneCleanII (Bio101) in accordance with the user's manual. The fragments obtained in this manner were cloned to SacI or SmaI of pBluescript II (Stratagene), and transformed in *E. coli* JM109 in accordance with a conventional method to prepare two types of libraries (SacI library and StuI library).

(5) Colony Hybridization and Sequencing

Primer 1 described in Table 1 was labeled with the DIG labeling kit of Boehringer Mannheim and the target genes were obtained by screening the above-mentioned two types of libraries. Colony hybridization was performed in accordance with the manual of Boehringer Mannheim at 60° C. About 50 positive colonies were obtained as a result of screening about 2,000 colonies. The plasmid DNA prepared from the positive colonies was allowed to react according to the Dye Terminator method, and sequencing was performed in accordance with a conventional method using the 373A Sequencer (Perkin Elmer).

As a result of sequencing, a plasmid containing the SacI fragment screened from the SacI library, and a plasmid containing the StuI fragment screened from the StuI library had about 140 bp overlapping portions, and when those sequences were connected, an open reading frame existed of about 1 kbp. The amino acid sequence predicted from this gene retains a sequence that is commonly conserved in prenyl transferase.

(6) PCR Cloning of Open Reading Frame

In order to clone an entire length of an open reading frame, oligonucleotides having the sequences shown in Table 2 were prepared. For these primers, restriction enzyme sites were inserted in front of and in back of the open reading frame in expression plasmid pTrc99A in consideration of cloning.

TABLE 1

| Primer 1 | 5' | ATC<br>C | AGA<br>G | AGA<br>G | GGG | TTC<br>C G | CCC | ACA | GTC | (SEQ ID NO: 2) |
|---|---|---|---|---|---|---|---|---|---|---|
| Primer 2 | 5' | ATC<br>C G | GCG<br>C | TTC | CAG | ATC<br>C G<br>G | GTC | GAC | GAC | (SEQ ID NO: 3) |

TABLE 2

| Primer 3 | TAA | AGT | GTA | A<u>GC</u> | <u>CAT</u><br>NcoI | <u>GG</u>T | GCC | (SEQ ID NO: 4) |
|---|---|---|---|---|---|---|---|---|
| Primer 4 | GAA | GGC | C<u>GT</u> | <u>CGA</u><br>SalI | <u>C</u>GA | AGC | GGT | (SEQ ID NO: 5) |

Next, using the genomic DNA of *Thermus thermophilus* strain HB8 as a template, a PCR reaction was carried out using the reaction mixture shown in Table 3 and a thermal cycler (Perkin Elmer).

TABLE 3

PCR Reaction Mixture

| Genomic DNA | 0.1 | µg |
|---|---|---|
| 10x Amplitaq buffer (Takara Shuzo) | 10 | µl |
| dNTPs (1.25 mM each) | 1 | µl |
| Primer 3 (10 µM) | 1 | µl |
| Primer 4 (10 µM) | 1 | µl |
| Amplitaq DNA polymerase (Perkin Elmer) | 5 | units |
| Sterile water | | |
| Total | 100 | µl |

The PCR reaction mixture was allowed to react for 7 minutes at 72° C. after 35 cycles of 30 seconds at 94° C., 30 seconds at 60° C. and 1 minute at 72° C. The reaction mixture was subjected to electrophoresis on 0.8% agarose gel, and a desired length of (about 1 kbp) DNA fragment was purified using GeneClean II (Bio101) in accordance with the user's manual. The purified DNA fragment was digested with NcoI and SalI and ligated to pTrc99A by a commercially available ligation kit (Takara Shuzo). This recombinant plasmid was treated by introducing into *E. coli* JM109 in accordance with the CaCl$_2$ method, and a resulting *E. coli* was cultured at 37° C. in LB medium. Next, colonies that grew on the plate were cultured in 2 ml of LB liquid medium containing 50 µg/ml of ampicillin. Moreover, the plasmid was prepared according to the alkaline SDS method described in Current Protocols in Molecular Biology. Preparation of the recombinant plasmid was confirmed by sequencing. The prepared recombinant plasmid was named pTE3.

Example 2

Expression of Geranylgeranyl Diphosphate Synthase

It is known that when *E. coli* retaining plasmid PACYC-IB containing the known crtI gene (phytoen synthase gene) and crtB gene (phytoen unsaturase gene) of *Erwinia uredovora* is placed in the presence of a plasmid containing geranylgeranyl diphosphate synthase gene, the *E. coli* cells turn red (J.B.C. 269, 20, 14792–14797 (1994)). This property can be used to confirm whether or not pTE3 has geranylgeranyl diphosphate synthase activity. Recombinant plasmid pTE3 obtained in Example 1 was transformed in accordance with a conventional method in pACYC-IB/DH5α. As a result, since a transformant exhibited a red color, it was determined to have geranylgeranyl diphosphate synthase activity.

Recombinant plasmid pTE3 was transformed in *E. coli* JM105 competent cells. After culturing the resulting transformant overnight at 37° C. in 20 ml of LB medium containing 50 µg/ml of ampicillin, it was inoculated into 1 liter of LB medium and cultured until the cell concentration reached a klett value of 40 to 50. Next, 10 ml of 100 mM IPTG were added followed by additional culturing for 4 hours. After culturing, the cells were collected and suspended in 100 ml of 50 mM Tris HCl (pH 7.0), 10 mM 2-mercaptoethanol and 1 mM EDTA solution. The resulting cell suspension was applied to an ultrasonic homogenizer (Tomy) to homogenize the cells followed by incubating for 1 hour at 55° C. to deactivate the protease derived from the *E. coli* cells. After centrifugation (8,000 rpm×10 min), the resulting supernatant was used for GGPP synthesis. Measurement of activity was performed using the reaction mixture composition shown in Table 4 using the RI trace method (J. Biochem., 113, 355–363 (1993)).

TABLE 4

| 1M Tris HCl (pH 8.5) | 50 | µl |
|---|---|---|
| 1M MgCl$_2$ | 5 | µl |
| 1M NH$_4$Cl | 50 | µl |
| 1M 2-mercaptoethanol | 50 | µl |
| 50 µM FPP* or DMAPP** | 50 | µl |
| 9.4 µM [$^{14}$C]-IPP (57 ci/mol) | 50 | µl |
| Crude enzyme preparation | 200 | µl |
| Sterile water | 545 | µl |
| Total | 1 | ml |

*FPP: Farnesyl diphosphate synthase
**DMAPP: Dimethylallylic diphosphate
IPP: Isopentenyl diphosphate Namely, after reacting the above-mentioned reaction mixture for 80 minutes at 55° C., 1 ml of saturated NaCl solution was added, and unreacted substrate was extracted using 3 ml of ether. Moreover, the reaction mixture was extracted with 3 ml of butanol, and after treating with potato acid phosphatase, it was extracted with pentane and the product was analyzed by TLC. TLC was developed with acetone/water (9/1) using reverse LKC-18 thin layer chromatography (Wattman). Those results are shown in FIG. 1.

As is clear from FIG. 1, the enzyme of the present invention clearly synthesized geranylgeranyl diphosphate from both of the substrates tested.

Example 3

Production of Geranylgeranyl Diphosphate Synthase Mediated by Fused Protein (1) Preparation of Glutathione S Transferase Fused Protein Plasmid Recombinant plasmid was prepared using commercially available fused protein vector pGEX-2T (Pharmacia). The ends of the PCR product described in part (6) of Example 1 were blunt-ended using a blunting kit of Takara Shuzo, and ligated to the SmaI site of pGEX-2T. Blunt-ending and ligation were performed according to the manual of Takara Shuzo. The resulting reaction mixture was used to transform *E. coli* JM109 in accordance with a conventional method. Transformant that grew at 37° C. were cultured in 2 ml of LB medium containing 50 µg/ml of ampicillin, the plasmid was prepared by alkaline SDS, and preparation of the recombinant plasmid was confirmed by sequencing. The prepared recombinant plasmid was named pTE7.

When pTE7 was transformed in *E. coli* pACYC-IB/DH5α in accordance with a conventional method in the same manner as for pTE20 and pTE3, since its transformant exhibited a red color, it was confirmed to have geranylgeranyl diphosphate synthase activity.

(2) Purification of Glutathione S Transferase Fusion Protein pTE7 obtained in part (1) of Example 3 was used to express enzyme in large volume in the same manner as Example 2. Namely, pTE7 was transformed in *E. coli* JM109, and after the resulting transformant was cultured overnight at 37° C. in 20 ml of LB medium containing 50

μg/ml of ampicillin, it was inoculated into 1 liter of LB medium and cultured until the cell concentration reached a klett value of 40 to 50. Next, 10 ml of 100 mM IPTG was added followed by additional culturing for 4 hours. After culturing, the cells were separated from 1 ml of culture by centrifugation (14,000 rpm, 10 min) and applied to SDS-polyacrylamide gel electrophoresis (SDS-page) in accordance with the method described in Current Protocols in Molecular Biology. As a result, fused protein in the vicinity of about 70 kD was confirmed to be expressed.

The remaining approximately 1 liter of culture was similarly separated by centrifugation (8,000 rpm, 10 min), the cells were collected and suspended in 50 ml of PBS buffer described in Current Protocols in Molecular Biology. This suspension was applied to an ultrasonic homogenizer (Tomy), and after homogenizing the cells, the product was separated into a supernatant fraction and precipitate fraction by centrifugation (4° C., 12,000 rpm).

50 ml of the supernatant fraction thus obtained was adsorbed onto a column packed with glutathione Sepharose 4B (Pharmacia), and eluted according to the Pharmacia protocol for glutathione Sepharose 4B to purify the enzyme. 2.5 ml of the eluent were desalted using a PD-10 column (Pharmacia). The resulting fusion protein (0.5 mg/ml) was cleaved with 2 units of thrombin (Boehringer Mannheim) to release the GGPS. Each of the elution fractions purified with glutathione Sepharose B along with the sample obtained following cleavage with thrombin were confirmed to be purified by performing SDS-page in the same manner as the above-mentioned sample.

(4) Measurement of Activity of Glutathione S Transferase Fused Protein

The enzyme activity of the free protein was measured by measurement of orthophosphate and pyrophosphate according to the Grindey-Nichol method (Grindey & Nichol, Anal. Biochem., 33, 114–119 (1970)). Namely, reaction was performed for 1 hour at 70° C. in the reaction solution shown in Table 5.

TABLE 5

| Enzyme Reaction Solution | | |
|---|---|---|
| 1M Tris HCl (pH 8.5) | 50 | μl |
| 1M MgCl$_2$ | 5 | μl |
| 1M NH$_4$Cl | 50 | μl |
| 1M 2-mercaptoethanol | 50 | μl |
| 50 nM FPP | 50 | μl |
| 50 nM IPP | 50 | μl |
| Enzyme | 200 | μg |
| Sterile water | | |
| Total | 1 | ml |

The reaction was stopped by adding 300 μl of water-saturated phenol and stirring well. After centrifuging (14,000 rpm, 5 min), 800 μl of the resulting supernatant was measured for the amount of orthophosphate and pyrophosphate in the reaction mixture using the Grindey-Nichol method. The specific activity of the purified enzyme according to the Grindey-Nichol method was 260 nmol/min·mg.

In addition, the activity of this enzyme was also measured using the RI trace method.

TABLE 6

| 1M Tris HCL (pH 8.5) | 10 | μl |
|---|---|---|
| 0.5 mM DMAPP or GPP or FPP | 50 | μl |

TABLE 6-continued

| 0.5 mM [$^{14}$C]-IPP (1 ci/mol) | 50 | μl |
|---|---|---|
| 0.1M MgCl$_2$ | 10 | μl |
| Enzyme | 2 | μg |
| Sterile water | 200 | μl |

After reacting for 30 minutes at 70° C., 200 μl of saturated saline and 1 ml of water-saturated 1-butanol were added followed by centrifuging for 1 minute at room temperature and 15,000 rpm. Potato acid phosphatase was added followed by incubating overnight at 37° C. 50 μl of GGOH was added, and after extracting with 3 ml of pentane, the product was analyzed by TLC. TLC was developed with acetone/water (9/1) using reverse LKC-18 thin layer chromatography (Whatman).

The specific activity was 106 nmol/min·mg.

(5) Preparation of Poly-His Fusion Protein Plasmid

Recombinant plasmid was prepared using commercially available fused protein vector pTrcHisB (Invitrogen). After treatment of the pTE7 described in part (1) of Example 3 with restriction enzymes BamHI and SalI, the resulting DNA fragment was ligated to the BamHI-XhoI sites of pTrcHisB. *E. coli* JM109 competent cells (Takara Shuzo) were transformed with the ligation mixture in accordance with a conventional method. The resulting transformant was cultured in 2 ml of LB medium, the plasmid was prepared by alkaline SDS, and preparation of the recombinant plasmid was confirmed by sequencing. The recombinant plasmid thus prepared was named pTE20.

(6) Expression of Poly-His Fused Protein

*E. coli* JM109 was transformed with pTE20, and after culturing overnight at 37° C. in 20 ml of LB medium, it was inoculated into 1 liter of LB medium containing 50 μg/ml of ampicillin, and cultured until the cell concentration reached a klett value of 40 to 50. Next, 10 ml of 100 mM IPTG were added followed by additional culturing for 4 hours. Analysis of the expressed enzyme was performed by SDS-polyacrylamide electrophoresis (SDS-page) in the same manner as part (4) of Embodiment 3. As a result, the fused protein was determined to be expressed in the vicinity of about 40 kD.

Namely, cells were collected by centrifugation of 1 ml of culture (14,000 rpm, 10 min), and applied to SDS-page (Tefco) in accordance with the method described in Current Protocols in Molecular Biology. After staining with Coumassey's brilliant blue, the gel was dried with a gel dryer made by Bio Rad.

The present invention enables enzyme having high levels of stability and activity unlike in the past to be produced in large amount by cloning of a thermostable GGPP synthase gene of *Thermus thermophilus* origin.

I claim:

1. An isolated DNA coding for geranylgeranyl diphosphate synthase, which can hybridize with the nucleotide sequence indicated in SEQ ID NO:1, in a hybridization medium comprising 5×SSC, blocking reagent 1% (w/v), N-lauroylsarcosine 0.1% (w/v), and SDS 0.02% (w/v), wherein the specific activity of said geranylgeranyl diphosphate synthase is at least 106 nmol/min/mg of protein as measured by an RI trace method.

2. An expression vector comprising the DNA according to claim 1.

3. A host cell transformed with the expression vector according to claim 2.

4. A process for producing geranylgeranyl diphosphate synthase having a specific activity at least 106 nmol/min/mg of protein as determined by an RI trace method comprising the steps of:
   culturing in medium host cells transformed with an expression vector comprising the isolated DNA according to claim 1; and
   recovering said geranylgeranyl diphosphate synthase from the medium.

5. Isolated recombinant DNA according to claim 1 operably linked to a gene encoding glutathione S transferase wherein said recombinant DNA encodes a geranylgeranyl diphosphate synthase-glutathione S transferase fusion protein having a specific activity of at least 106 nmol/min/mg as measured by RI trace method.

6. A recombinant plasmid comprising the DNA according to claim 5.

7. A method for producing a fusion protein comprising geranylgeranyl diphosphate and glutathione S transferase comprising:
   culturing in medium host cells transformed with the recombinant plasmid of claim 5; and
   recovering said fusion protein from the medium; wherein said fusion protein has a specific activity of at least 106 nmol/min/mg as measured by RI trace method.

8. A host cell transformed with the recombinant plasmid according to claim 6.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 1035 base pairs
       (B) TYPE: nucleic acid
       (C) STRANDEDNESS: single
       (D) TOPOLOGY: linear (ii) MOLECULE TYPE: genomic DNA (xi) SEQUENCE DESCRIPTION: SEQ ID NO:1:

| | | | | | |
|---|---|---|---|---|---|
| ATGGTGCCCG | CGCCCGAGAC | CATCCGGCAG | GCCCTCCAAG | AAAGGCTCAT | CGCCCGCCTG | 60 |
| GACCACACCG | ACCCCCTTTA | CCGGGACCTC | CTCCAGGACT | ACCCGAGACG | GGGGGGAAAG | 120 |
| ATGCTCCGGG | GCCTTCTCAC | CGTGTACAGC | GCCCTGGCCC | ACGGGGCGCC | CTTGGAAGCG | 180 |
| GGCCTCGAGA | CCGCGACCGC | CCTGGAGCTC | TTCCAGAACT | GGGTCCTGGT | CCACGACGAC | 240 |
| ATTGAGGACG | GCTCCGAGGA | GCGCCGGGGC | CGGCCCGCCC | TCCACCGTCT | CCACCCCATG | 300 |
| CCCCTGGCCC | TGAACGCGGG | GGACGCCATG | CACGCCGAGA | TGTGGGGCCT | CCTCGCGGAA | 360 |
| GGCCTCGCCC | GGGGGCTTTT | CCCCCCGGAG | GTCCTCTTGG | AGTTCCACGA | GGTGGTGCGC | 420 |
| CGCACCGCCT | ACGGTCAGCA | CCTGGACCTC | CTCTGGACCC | TCGGTGGGAC | CTTTGACCTG | 480 |
| AGGCCGGAGG | ACTACTTCCG | CATGGTGGCC | CACAAGGCCG | TCTACTACAC | CGCCGTGGTC | 540 |
| CCCCTGCGCC | TCGGGGTCCT | TCTCGTCGGG | AAGACCCCGC | CGCCGCCCTA | CGAGGAGGGG | 600 |
| GGGCTTAGGC | TGGGGACGGC | CTTCCAGATC | GTGGACGACG | TCTTGAACCT | GGAAGGGGGG | 660 |
| GAGGCCTACG | GGAAGGAAAG | GACCGGGGAC | CTCTACGAGG | GCAAGCGCAC | CCTGATCCTC | 720 |
| CTCCGCTTCC | TGGAGGAGAC | CCCGCCCGAG | GAAAGAGCCC | GGGAGGCGAA | GCCCGAGGCG | 780 |
| GAGGTAGGTT | GGCTTCTGGA | AAGGCTCCTC | GCCTCGAGGG | CCCTGGCCTG | GACAAGGCG | 840 |
| GAGGCCAAGC | GCCTCCAGGC | CGAGGGCCTC | GCCCTCCTGG | AGGCCGCCTT | CCAGGACCTC | 900 |
| CCGGGAAGGA | GGCCTGGACC | ACCTCCGCGG | TCTCCTCGCC | GCTTTGGTGG | AGCGCAGGGC | 960 |
| ATAATGGGGC | CATGCAGGGG | GTGCGCTTCC | GGGTCATCAC | CGCCAACGAC | CCCGACATCC | 1020 |
| TCCAAGAGCG | CCTGA | | | | | 1035 |

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: genomic DNA (xi) SEQUENCE DESCRIPTION: SEQ ID NO:2:

MTCAGRAGRG GGYTSCCCAC AGTC                                    24

(2) INFORMATION FOR SEQ ID NO:3:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: genomic DNA (xi) SEQUENCE DESCRIPTION: SEQ ID NO:3:

MTSGCSTTCC AGVTSGTCGA CGAC                                              24

(2) INFORMATION FOR SEQ ID NO:4:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: genomic DNA (xi) SEQUENCE DESCRIPTION: SEQ ID NO:4:

TAAAGTGTAA GCCATGGTGC C                                                 21

(2) INFORMATION FOR SEQ ID NO:5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: genomic DNA (xi) SEQUENCE DESCRIPTION: SEQ ID NO:5:

GAAGGCCGTC GACGAAGCGG T                                                 21

(2) INFORMATION FOR SEQ ID NO:6:

(i) SEQUENCE CHARACTERISTICS:
            (A) LENGTH: 344 amino acids
            (B) TYPE: amino acids
            (C) STRANDEDNESS: single
            (D) TOPOLOGY: linear (ii) MOLECULE TYPE: Protein (xi) SEQUENCE DESCRIPTION: SEQ ID NO:6:

Met Val Pro Ala Pro Glu Thr Ile Arg Gln Ala Leu Gln Glu Arg Leu
                  5                  10                  15

Ile Ala Arg Leu Asp His Thr Asp Pro Leu Tyr Arg Asp Leu Leu Gln
             20                  25                  30

Asp Tyr Pro Arg Arg Gly Gly Lys Met Leu Arg Gly Leu Leu Thr Val
             35                  40                  45

Tyr Ser Ala Leu Ala His Gly Ala Pro Leu Glu Ala Gly Leu Glu Thr
         50                  55                  60

Ala Thr Ala Leu Glu Leu Phe Gln Asn Trp Val Leu His Asp Asp
65                  70                  75                  80

Ile Glu Asp Gly Ser Glu Glu Arg Arg Gly Arg Pro Ala Leu His Arg
                 85                  90                  95

Leu His Pro Met Pro Leu Ala Leu Asn Ala Gly Asp Ala Met His Ala
                100                 105                 110

Glu Met Trp Gly Leu Leu Ala Glu Gly Leu Ala Arg Gly Leu Phe Pro
            115                 120                 125

Pro Glu Val Leu Leu Glu Phe His Glu Val Val Arg Arg Thr Ala Tyr
        130                 135                 140

Gly Gln His Leu Asp Leu Leu Trp Thr Leu Gly Gly Thr Phe Asp Leu
145                 150                 155                 160

Arg Pro Glu Asp Tyr Phe Arg Met Val Ala His Lys Ala Val Tyr Tyr

-continued

```
              165                 170                 175
Thr Ala Val Val Pro Leu Arg Leu Gly Val Leu Leu Val Gly Lys Thr
            180                 185                 190

Pro Pro Ala Ala Tyr Glu Glu Gly Gly Leu Arg Leu Gly Thr Ala Phe
            195                 200                 205

Gln Ile Val Asp Asp Val Leu Asn Leu Glu Gly Gly Glu Ala Tyr Gly
            210                 215                 220

Lys Glu Arg Thr Gly Asp Leu Tyr Glu Gly Lys Arg Thr Leu Ile Leu
225                 230                 235                 240

Leu Arg Phe Leu Glu Glu Thr Pro Pro Glu Glu Arg Ala Arg Glu Ala
                245                 250                 255

Lys Pro Glu Ala Glu Val Gly Trp Leu Leu Glu Arg Leu Leu Ala Ser
                260                 265                 270

Arg Ala Leu Ala Trp Asp Lys Ala Glu Ala Lys Arg Leu Gln Ala Glu
            275                 280                 285

Gly Leu Ala Leu Leu Glu Ala Ala Phe Gln Asp Leu Pro Gly Arg Arg
            290                 295                 300

Pro Gly Pro Pro Pro Arg Ser Pro Arg Arg Phe Gly Gly Ala Gln Gly
305                 310                 315                 320

Ile Met Gly Pro Cys Arg Gly Cys Ala Ser Gly Ser Ser Pro Pro Thr
                325                 330                 335

Thr Pro Thr Ser Ser Lys Ser Ala
                340
```